United States Patent [19]
Swindle et al.

[11] Patent Number: 5,891,017
[45] Date of Patent: Apr. 6, 1999

[54] SURGICAL STABILIZER AND METHOD FOR ISOLATING AND IMMOBILIZING CARDIAC TISSUE

[75] Inventors: Carl A. Swindle, Dana Point, Calif.; Robert Joseph Todd, Salt Lake City, Utah

[73] Assignee: Baxter Research Medical, Inc., Midvale, Utah

[21] Appl. No.: 853,099

[22] Filed: May 7, 1997

Related U.S. Application Data

[60] Provisional application No. 60/034,888 Jan. 31, 1997.
[51] Int. Cl.$^6$ .................................................. A61B 17/00
[52] U.S. Cl. .......................... 600/205; 600/219; 600/235; 600/201
[58] Field of Search .................................... 600/201, 204, 600/205, 210, 219, 235; 606/205, 207, 208, 206, 1; 128/898

[56] References Cited

U.S. PATENT DOCUMENTS

| | | | |
|---|---|---|---|
| 1,664,112 | 3/1928 | Junemann | 606/205 X |
| 2,082,782 | 6/1937 | Allen | 606/205 X |

(List continued on next page.)

FOREIGN PATENT DOCUMENTS

| | | |
|---|---|---|
| 646357 | 4/1995 | European Pat. Off. . |
| 791329 | 8/1997 | European Pat. Off. . |
| 791330 | 8/1997 | European Pat. Off. . |
| 9320139.7 | 4/1994 | Germany . |
| 4300307 | 7/1994 | Germany . |
| 970751 | 2/1997 | Norway . |
| 970753 | 2/1997 | Norway . |
| 736949 | 5/1980 | Russian Federation . |
| WO 93/08867 | 5/1993 | WIPO . |
| WO 94/21179 | 9/1994 | WIPO . |
| WO 96/16604 | 7/1996 | WIPO . |
| 97/10753 | 3/1997 | WIPO . |
| 97/40738 | 11/1997 | WIPO . |

OTHER PUBLICATIONS

Borst et al., Coronary Artery Bypass Grafting Without Cardiopulmonary Bypass and Without Interuption of Native Coronary Flow Using a Novel Anastomosis Site Restraining Device ("Octopus"), Journal of the American College of Cardiology, vol. 27, No. 6., May 1996.

Borst, C. et al., Regional Cardiac Wall Immobilization for Open Chest and Closed Chest Coronary Artery Bypass Grafting on the Beating Heart: The 'Octopus' Method, Abstracts from the 68th Scientific Session, vol. 92, No. 8, p. 848.

Grundeman, P.F. et al., Thoracoscopic Creation of Transmural Laser Channels in the Beating Porcine Heart Using Conventional Medical Lasers: Closed Chest Application of the Utrecht 'Octopus' Cardiac Immobilization Method, Abstracts from the 69th Scientific Sessions, vol. 94 (8 Supplement), No. 2792, 1996.

(List continued on next page.)

Primary Examiner—Jeffrey A. Smith
Attorney, Agent, or Firm—Workman, Nydegger & Seeley

[57] ABSTRACT

The present invention is directed to new and useful methods and apparatus for isolating and immobilizing tissue for improved presentation in a surgical site, preferably in coronary bypass on a beating heart. At the same time, the present invention also helps avert ischemic damage to tissues downstream. A surgical stabilizer in accordance with the present invention offers physical manipulation of a surgical site, which improves the surgeon's sewing, grasping, and visualizing abilities at the site, and in turn, may increase the confidence and patency of the graft. The stabilizer is used to compress or to suction a region of the heart just below a stenotic coronary artery. The surgeon may selectively articulate the tissue by spreading it apart or pushing it together, as per his or her preference, or per the requirements of the surgical situation. The surgeon may lock in place the handle via a ratchet mechanism to hold the specific open or closed articulation of the surgical stabilizer. With the tissue thus isolated and immobilized, the surgeon may then graft the bypass vessel distal to the stenosis in the coronary artery.

21 Claims, 6 Drawing Sheets

U.S. PATENT DOCUMENTS

| | | | |
|---|---|---|---|
| 3,503,396 | 3/1970 | Pierie et al. | 606/207 |
| 4,655,219 | 4/1987 | Petruzzi | 128/321 |
| 4,944,741 | 7/1990 | Hasson | 606/206 |
| 5,002,543 | 3/1991 | Bradshaw et al. | 606/62 |
| 5,089,007 | 2/1992 | Kirsch et al. | 606/205 |
| 5,152,279 | 10/1992 | Wilk . | |
| 5,178,133 | 1/1993 | Pena . | |
| 5,195,505 | 3/1993 | Josefsen . | |
| 5,195,506 | 3/1993 | Hulfish . | |
| 5,224,954 | 7/1993 | Watts et al. | 606/205 |
| 5,235,966 | 8/1993 | Jamner . | |
| 5,245,987 | 9/1993 | Redmond et al. . | |
| 5,267,554 | 12/1993 | Wilk . | |
| 5,271,385 | 12/1993 | Bailey . | |
| 5,275,608 | 1/1994 | Forman et al. | 606/170 |
| 5,280,782 | 1/1994 | Wilk . | |
| 5,282,826 | 2/1994 | Quadri | 606/207 |
| 5,284,128 | 2/1994 | Hart . | |
| 5,306,234 | 4/1994 | Johnson | 604/49 |
| 5,308,327 | 5/1994 | Heaven et al. | 604/96 |
| 5,339,801 | 8/1994 | Poloyko et al. . | |
| 5,339,802 | 8/1994 | Cook . | |
| 5,390,664 | 2/1995 | Redmond et al. . | |
| 5,400,773 | 3/1995 | Zhu et al. . | |
| 5,431,662 | 7/1995 | Nicholas | 606/119 |
| 5,452,733 | 9/1995 | Sterman et al. | 128/898 |
| 5,456,695 | 10/1995 | Dallemagne | 606/207 |
| 5,474,056 | 12/1995 | Laborie et al. | 600/214 |
| 5,474,571 | 12/1995 | Lang | 606/205 |
| 5,490,819 | 2/1996 | Nicholas et al. | 600/201 |
| 5,507,773 | 4/1996 | Huitema et al. | 606/207 |
| 5,514,148 | 5/1996 | Smith, III. | 606/151 |
| 5,514,156 | 5/1996 | Schulze et al. | 606/205 |
| 5,514,157 | 5/1996 | Nicholas et al. | 606/206 |
| 5,520,678 | 5/1996 | Heckele et al. | 606/1 |
| 5,554,101 | 9/1996 | Matula et al. | 600/214 |
| 5,562,640 | 10/1996 | McCabe et al. | 604/280 |
| 5,562,700 | 10/1996 | Huitema et al. | 606/207 |
| 5,562,702 | 10/1996 | Huitema et al. | 606/207 |
| 5,569,274 | 10/1996 | Rapacki et al. | 606/158 |
| 5,571,215 | 11/1996 | Sterman et al. | 623/66 |
| 5,588,951 | 12/1996 | Zhu et al. | 600/207 |
| 5,607,450 | 3/1997 | Zvenyatsky et al. | 606/206 |
| 5,611,813 | 3/1997 | Lichtman | 606/205 |
| 5,613,937 | 3/1997 | Garrison et al. | 600/201 |
| 5,620,458 | 4/1997 | Green et al. | 606/198 |
| 5,620,459 | 4/1997 | Lichtman | 606/205 |
| 5,649,957 | 7/1997 | Levin | 606/207 |
| 5,690,606 | 11/1997 | Slotman | 600/206 |
| 5,727,569 | 3/1998 | Benetti et al. | 128/898 |
| 5,749,892 | 5/1998 | Vierra et al. | 600/201 X |
| 5,782,746 | 7/1998 | Wright | 600/37 |
| 5,807,243 | 9/1998 | Vierra et al. | 600/204 |

OTHER PUBLICATIONS

Jansen Erik W.L., et al., Less Invasive Coronary Artery Bypass Grafting on the Beating Heart: Initial Clinical Experience with the Utrecht 'Octopus' Method for Regional Cardiac Wall Immobilization, Supplement I, Circulation vol. 94, No. 8, Oct. 15, 1996.

Borst C., Microsurgical Coronary Artery End–to–Side Anastomosis on the Beating Heart Without Interruption of Coronary Flow: Feasibility Study in the Pig, JACC, vol. 27, Abstracts, 44A, 1996.

Gründeman P.F., Thoracoscopic Creation of Transmural Laser Channels in the Beating Porcine Heart Using Conventional Lasers: Closed Chest Application of the 'Octopus' Cardiac Immobilization Method, European Heart Journal, vol. 17, p. 136, abstr. suppl. (806), 1996.

Isik O., Complete Myocardial Revascularization With Left Heart Bypass Without Using Oxygenator on the Beating Heart, European Heart Journal, vol. 17, p. 138, abstr. suppl. (811), 1996.

Jansen E.W.L., Less Invasive Coronary Artery Bypass Grafting on the Human Beating Heart Using the Utrecht 'Octopus' Selective Immobilization Method, European Heart Journal, vol. 17, p. 138, abstr. suppl, (812), 1996.

Thibault W.N., Three–day Coronary Artery Bypass Graft Surgery: Outcomes, European Heart Journal, vol. 17, p. 138, abstr. suppl. (813), 1996.

Hennessy T., Determinants of Survival in Patients Post Bypass Surgery for Isolated Stenosis on the left Anterior Descending Coronary Artery, European Heart Journal, vol. 17, p. 138, abstr. suppl. (814), 1996.

Borst C. et al., Coronary Artery Bypass Grafting Without Cardiopulmonary Bypass and Without Interruption of Native Coronary Flow Using a Novel Anastomosis Site Restraining Device ("Octopus"), JACC, vol. 27, No. 6, pp. 1356–1364, May 1996.

Acuff T.E. et al., Minimally Invasive Coronary Artery Bypass Grafting, Ann. Thorac. Surg., 61:135–7, 1996.

Subramanian V.A., Less Invasive Arterial CABG on a Beating Heart, Ann. Thorac. Surg., 63:S68–71, 1997.

Boonstra P.W., et al., Local Immobilization of the Left Anterior Descending Artery for Minimally Invasive Coronary Bypass Grafting, Ann. Thorac. Surg., 63:S76–8, 1997.

Cremer J. et al., Off–Bypass Coronary Bypass Grafting via Minithoracotomy Using Mechanical Epicardial Stabilization, Ann. Thorac. Surg., 63:S79–83, 1997.

Gründeman P.F., Hemodynamic Changes During Displacement of the Beating Heart by the Utrecht Octopus Method, Ann. Thorac. Surg., 63:S88–92, 1997.

Mack, M.J. et al., Video–Assisted Coronary Bypass Grafting on the Beating Heart, Ann. Thorac. Surg., 63:S100–3, 1997.

Calafiore A. M., et al., Minimally Invasive Coronary Artery Surgery: The Last Operation, Seminars in Thoracic and Cardiovascular Surgery, vol. 9., No. 4, pp. 305–311, Oct. 1997.

Borst C. et al., Less Invasive Artery Bypass and via Reduced Surgical Access, Heart, 77:302–303, 1997.

John A. Rousou, M.D.; Richard M. Engelman, M.D.; Josef E. Flack, III, M.D.; and, David W. Deaton, M.D., "*Cardiac Retractor for Coronary Bypass Operations,*" Ann. Thorac. Surg. 1991; 52:877–878.

G.D. Angelina, M.D., "*A Simple, Inexpensive Method of Heart Retraction During Coronary Artery Bypass Surgery,*" Ann Thorac Surgery 46:246–267, Aug., 1988.

Erik W.J. Jansen, M.D.; Paul F. Grundeman, M.D.; Hendricus J. Mansvelt Beck; Robin H. Heijmen, M.D.; and, Cornelius Borst, M.D., "*Experimental Off–Pump Grafting of a Circumflex Branch via Sternotomy Using a Suction Device,*" Ann Thorac Surg 1997; 63:S93–96.

Cornelius Borts; Erik W.L. Jansen; and Paul F. Grundeman, "*Less Invasive Coronary Artery Bypass Grafting: Without Cardiopulmonary Bypass and Via Reduced Surgical Access,*" Heart 1997; 77:302–303.

SURGICAL STABILIZER AND METHOD FOR ISOLATING AND IMMOBILIZING CARDIAC TISSUE

BACKGROUND OF THE INVENTION

1. The Field of the Invention

The present invention is directed generally to methods and apparatus for stabilizing a surgical site and more specifically to methods and apparatus for isolating and immobilizing a surgical site during cardiac surgical procedures.

2. Related Application

Benefit of the earlier filing date of Provisional Patent application Ser. No. 60/034,888, filed Jan. 31, 1997, is claimed for this application under Section 119(e) of Title 35 of the United States Code.

3. The Relevant Technology

Throughout many surgical procedures, and especially surgical procedures involving the heart, anatomical and physiological constraints often impede the surgical process. For example, in cardiac surgical procedures, the requisite surgical site is often difficult to access and manage. Anatomically, the heart is well protected by the sternum, the rib cage, and multiple layers of connective tissues, and thus often necessitates arduous dissection. Physiologically, a beating heart presents anything but a stable surgical field. As a result, procedures such as coronary artery bypass on a beating heart demonstrate distinct surgical barriers.

Coronary artery bypass surgery is commonly required when coronary arteries narrowed by cholesterol-rich fatty deposits or plaque are unable to supply the heart muscle with a sufficient amount of blood, and as a result, the heart becomes starved for oxygen. Left untreated, coronary artery disease ultimately leads to acute myocardial infarction, or heart attack. In coronary artery bypass surgery, a surgeon grafts a section of a healthy vessel to bypass a stenotic or partially blocked portion of a coronary artery in order to ameliorate the oxygen supply to the heart muscle.

In many cases, coronary bypass surgery may be performed on a beating heart. This eliminates some of the risks, such as ischemic damage to the heart or peripheral tissues, and exposure of the blood to extracorporeal circulation, tubing, filters and oxygenators associated with procedures wherein the heart is stopped. However, in coronary bypass on a beating heart, surgeons have traditionally encountered difficulty isolating and immobilizing the diseased coronary arteries. Essentially, every beat of the heart results in movement at the site of the bypass which disrupts the surgery and may even damage the bypass graft.

In order to secure the surgical site, surgeons have conventionally performed tamponade, or compression of the heart, by utilizing devices that press down on the tissue at the surgical site. Yet such an approach lacks precise isolation of the coronary artery and diminishes access thereto. Alternatively, surgeons have utilized a pair of suction devices to pull the tissue surrounding and including a coronary artery slightly away from the heart. This approach offers tenuous stability and isolation of the surgical site at best.

SUMMARY AND OBJECTS OF THE INVENTION

It is therefore a primary object of the present invention to provide methods and apparatus to improve access to a cardiac surgical site during coronary artery bypass on a beating heart, or other repair to the heart.

It is another object of the present invention to provide methods and apparatus for isolation and immobilization of a cardiac surgical site during surgery on a beating heart.

It is still another object of the present invention to provide methods and apparatus to improve surgical presentation of a cardiac surgical site, either by articulating the tissue apart or together.

Yet another object of the present invention is to provide methods and apparatus to improve compression, or tamponade, of cardiac tissue.

Still another object of the present invention is to provide methods and apparatus to improve retraction of cardiac tissue.

Another object of the present invention is to provide methods and apparatus to improve access to and isolation of a coronary artery, without substantially impeding the flow of oxygenated blood to the heart muscle during coronary artery by-pass surgery.

Another object of the present invention is to provide in one device, immobilization, presentation, and isolation of a cardiac surgical site.

These and other objects and advantages of the invention will be better understood by reference to the detailed description, or will be appreciated by the practice of the invention.

To achieve the foregoing objects, and in accordance with the invention as embodied and broadly described herein, the present invention relates to an apparatus for isolating and immobilizing tissue for improved presentation in a surgical site, preferably in coronary bypass surgery on a beating heart. At the same time, the present invention helps avert ischemic damage to distal tissues. A surgical stabilizer in accordance with the present invention offers novel physical manipulation of the surgical site, which improves the surgeon's sewing, grasping, and visualizing abilities at the site, and in turn, may increase the confidence and patency of the graft.

The present invention is additionally directed to a method for using the surgical stabilizer. In a preferred embodiment of the present invention, the stabilizer is used to tamponade, or compress, a region of the heart around a stenotic coronary artery. Alternatively, a vacuum is utilized to suction the tissue around a stenotic coronary artery, which allows the surgeon to lift the anastomosis site for closer access thereto. The surgeon selectively spreads the tissue apart or pushes it together, as per his or her preference, or per the requirements of the surgical situation. The surgeon may lock in place the handle via a ratchet mechanism to hold the specific open or closed articulation of the surgical stabilizer. With the tissue thus isolated and immobilized, the surgeon may then graft the bypass vessel just distal to the stenosis in the coronary artery.

These and other objects and features of the present invention will become more fully apparent from the following description and appended claims, or may be learned by the practice of the invention as set forth hereinafter.

BRIEF DESCRIPTION OF THE DRAWINGS

In order to more fully understand the manner in which the above-recited and other advantages and objects of the invention are obtained, a more particular description of the invention will be rendered by reference to a specific embodiment thereof which is illustrated in the appended drawings. Understanding that these drawings depict only a typical embodiment of the invention and are not therefore to be considered to be limiting of its scope, the invention in its presently understood best mode for making and using the same will be described and explained with additional specificity and detail through the use of the accompanying drawings in which.

DETAILED DESCRIPTION OF THE PREFERRED EMBODIMENTS

The present invention relates to methods and apparatus for isolating and immobilizing tissue for improved presentation in a surgical site while averting ischemic damage to tissues downstream. For purposes of brevity and simplicity, the following discussion is directed to methods and apparatus for use in connection with coronary artery bypass on a beating heart, although it should be understood that such discussion is merely exemplary.

The coronary arteries, which branch immediately off of the ascending aorta as it exits the left ventricle, supply oxygenated blood to the heart muscle. These arteries are especially prone to developing fatty deposits or plaques that narrow the available diameter for blood flow to the heart, and can become so severe that the vessel is actually occluded. In turn, this causes a reduction in the amount of oxygen reaching the heart muscle, often resulting in myocardial ischemia, or myocardial infarction, commonly referred to as a heart attack.

It is possible to ameliorate this condition by attaching a vessel that circumvents or "bypasses" the blockage. In a procedure known as coronary artery bypass, a length of blood vessel, usually taken from the saphenous vein in the leg, is sutured to the aorta and to the coronary artery at a location beyond the site of the blockage, or stenosis. Alternatively the internal mammary artery or other native vessel is harvested intact and attached to the coronary artery just beyond, or distal to the stenosis.

In coronary artery bypass on a beating heart, anatomical and physiological constraints often impede the surgical process. Anatomically, the heart is well protected by the sternum, the rib cage, and layers of connective tissues, and thus may require arduous dissection. Physiologically, a beating heart offers an unstable surgical field; every beat of the heart causes movement at the site of the bypass, which disrupts the surgery and may even damage the bypass graft.

In order to secure the surgical site, surgeons have conventionally performed tamponade, or compression of the heart, by utilizing devices that press down on the cardiac tissue. Alternatively, surgeons have utilized suction devices to literally pull the tissue surrounding and including a coronary artery away from the heart. Neither conventional method, however, provides adequate isolation and immobilization of the surgical site. In addition, the conventional methods do not address the surgeon's need to manipulate tissue for improved surgical presentation.

Figure 1:
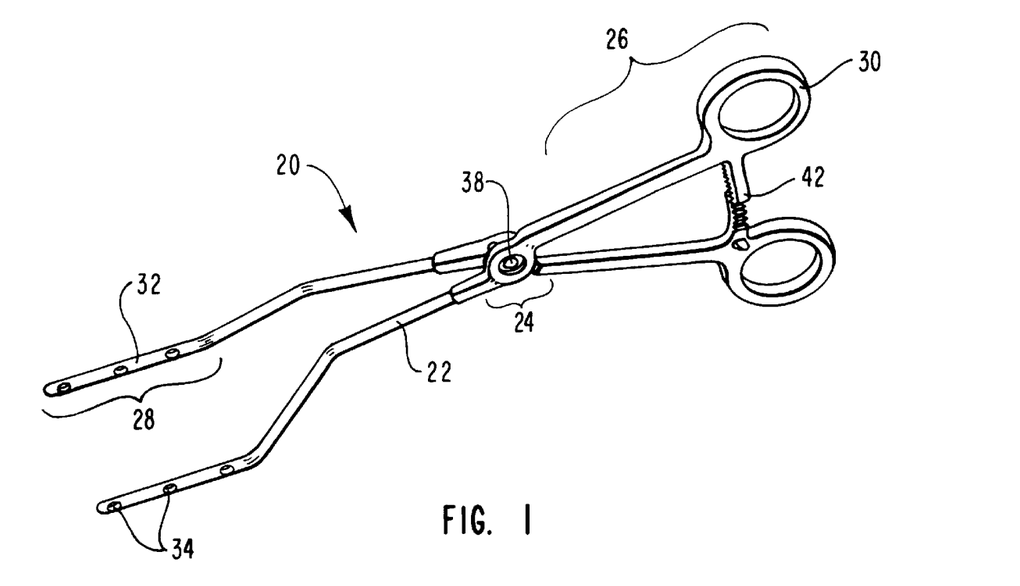
FIG. 1 is a perspective posterior view of one embodiment of the present invention.

By way of contrast, FIG. 1 illustrates features of the present invention that solve the problems encountered with conventional devices. A surgical stabilizer in accordance with the present invention offers immobilization and isolation of the surgical site and facilitates presentation thereof to the surgeon, while averting ischemic damage to downstream tissues. In addition, the physical manipulation provided by the present invention improves the surgeons's sewing, grasping, and visualizing abilities at the site, and in turn, may increase the confidence and patency of the graft.

FIG. 1 depicts one presently preferred embodiment of a surgical stabilizer generally labelled 20, for immobilizing and isolating a cardiac surgical site, and improved presentation thereof. Preferably, the cardiac stabilizer comprises substantially plastic materials, but is not limited thereto. The present invention may also be comprised of surgical steel, for example, or combinations of steel and plastic.

As illustrated in FIG. 1, the surgical stabilizer of the present invention preferably comprises two legs 22, articulation joint 24, and a handle 26. The handle 26 preferably comprises finger holes 30 providing one-handed manipulation of the surgical stabilizer. FIG. 1 illustrates a preferred embodiment of the finger holes of the handle. It should be understood, however, that alternate means for manipulating the surgical stabilizer, such as a rounded grip, would be within the scope of the present invention.

The legs 22 essentially slant downward from the handle 26 and terminate in projections, or feet 28. FIG. 1 illustrates a preferred embodiment of the feet 28 in relation with the legs 22 and the handle 26. In use, the feet 28 comprise the significant portion of the apparatus that comes into contact with cardiac tissue.

The posterior surface 32 of the feet preferably includes indentations 34 which serve as means for promoting traction of the feet on cardiac tissue by providing a slightly rough rather than slick posterior surface. In a preferred embodiment of the present invention illustrated in FIG. 1, the posterior surface 32 includes a plurality of indentations spaced substantially equally apart. It should be understood, however, that a greater or lesser number of indentations would be within the scope of the present invention. In addition, the indentations need not necessarily be spaced equidistant from one another.

It should also be appreciated that other means for promoting traction of the feet on cardiac tissue would be within the scope of the present invention. For example, any protrusions such as ridges or knobs, or embossed patterns on the posterior surface of the feet would also serve as means for promoting traction. In addition, the posterior surface of the feet may be sand-blasted, roughened or scored as means for promoting traction.

Figure 3:
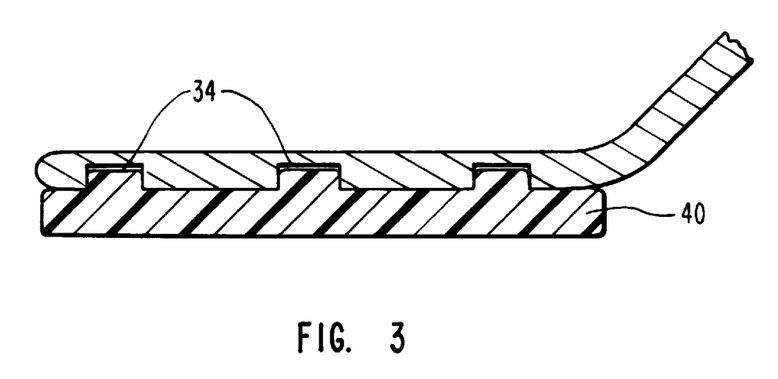
FIG. 3 is a partial side view of an alternate embodiment of FIG. 1.

In an alternate embodiment illustrated in FIG. 3, indentations 34 enable insertion of disposable traction devices 40 similar to those used with surgical clamps, which would be familiar to those of skill in the art. Such disposable traction devices include a rough or rugged surface that improves the gripping ability of the feet on the tissue.

It is a feature of the present invention that the feet 28 are utilized to tamponade, or compress, the cardiac tissue. With pressure exerted on the feet via manipulation of the handle in the direction of the cardiac tissue, the feet compress the tissue of the heart, and thus help to stabilize and immobilize the surgical site.

It is an additional feature of the present invention that the legs and feet preferably work in concert with one another. For example, any movement by one foot is mirrored by the other foot. In other words, in downward manipulation of the surgical stabilizer, the feet tamponade together. Such uniformity facilitates precise isolation of the surgical site, and also eliminates tissue distortion due to erratic or uneven manipulation of the tissue.

It is also a feature of the present invention that the legs and feet articulate uniformly with respect to one another. In the preferred embodiment of the present invention, the articulation of the feet is utilized to spread out cardiac tissue, or push cardiac tissue together. This offers distinct choices not heretofore available to the surgeon to physically manipulate the graft site, which ultimately leads to improved bypass grafting. In selectively being able to compress, articulate apart, and articulate together, the surgeon can access, grasp, and sew the bypass graft with improved efficiency and success.

FIG. 1 illustrates a preferred articulation mechanism represented by articulation joint 24. In a preferred embodiment, articulation joint 24 serves as the pivot which further facilitates a parallel response in the legs 22 when the handle 26 is manipulated. That is, when the handle is opened, the legs open. When the handle is closed, the legs close. In turn, the articulation joint allows a surgeon to selectively spread the tissue apart, or push the tissue together. Either position helps immobilize and isolate the surgical site in a manner not heretofore achieved in coronary bypass on a beating heart, resulting in improved surgical presentation.

Figure 7:
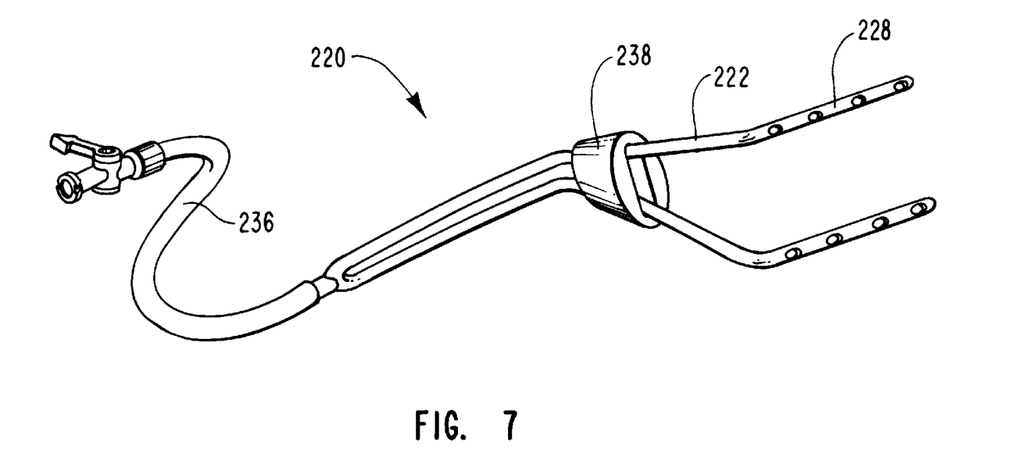
FIG. 7 is an alternate embodiment of the present invention.
Figure 8:
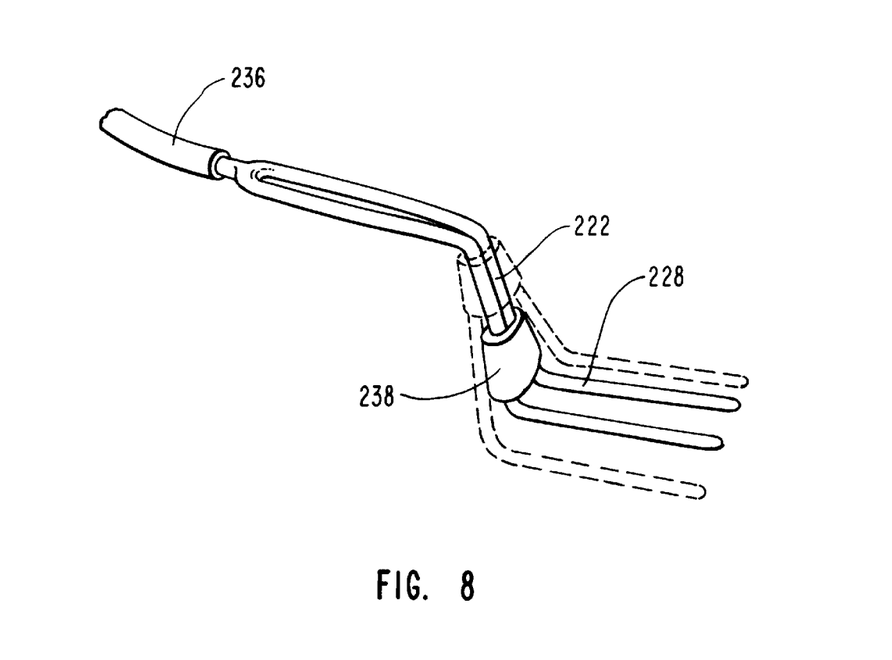
FIG. 8 is another view of the embodiment from FIG. 7.

In a preferred embodiment illustrated in FIG. 1, articulation joint comprises a pin mechanism 38. Alternatively, the articulation joint may comprise a hinge mechanism. It should be understood, however, that other means for articulating the legs would be within the scope of the present invention. For example, FIGS. 7 and 8 illustrate an embodiment wherein a non-hinged member such as a sleeve 238 moved up and down legs 222 causes the feet 228 to open or close in response.

In a preferred embodiment incorporating an articulation joint, it is also preferable that the handle comprises a ratchet mechanism 42 as illustrated in FIG. 1, such that upon articulation, the legs can be secured and maintained in an open or closed position. Furthermore, ratchet mechanism 42 is of a length that accommodates and secures the widest and the narrowest articulation positions of the legs.

Alternatively, the handle may include other means for retaining an articulated position, such as detents or mechanical stops, to secure and lock the articulated legs into place. It is an additional feature of the present invention that such means for retaining an articulated position are operated with only one hand.

The present invention is additionally directed to a method for using the surgical stabilizer. In a preferred embodiment, illustrated in FIG. 2, the surgical stabilizer 20 is used to tamponade a region of the heart 44 just proximal to a stenotic coronary artery. The surgeon selectively isolates and immobilizes the tissue by manipulating the surgical stabilizer to articulate the tissue apart or push it together, as per his or her preference, or per the requirements of the surgical situation.

Figure 2:
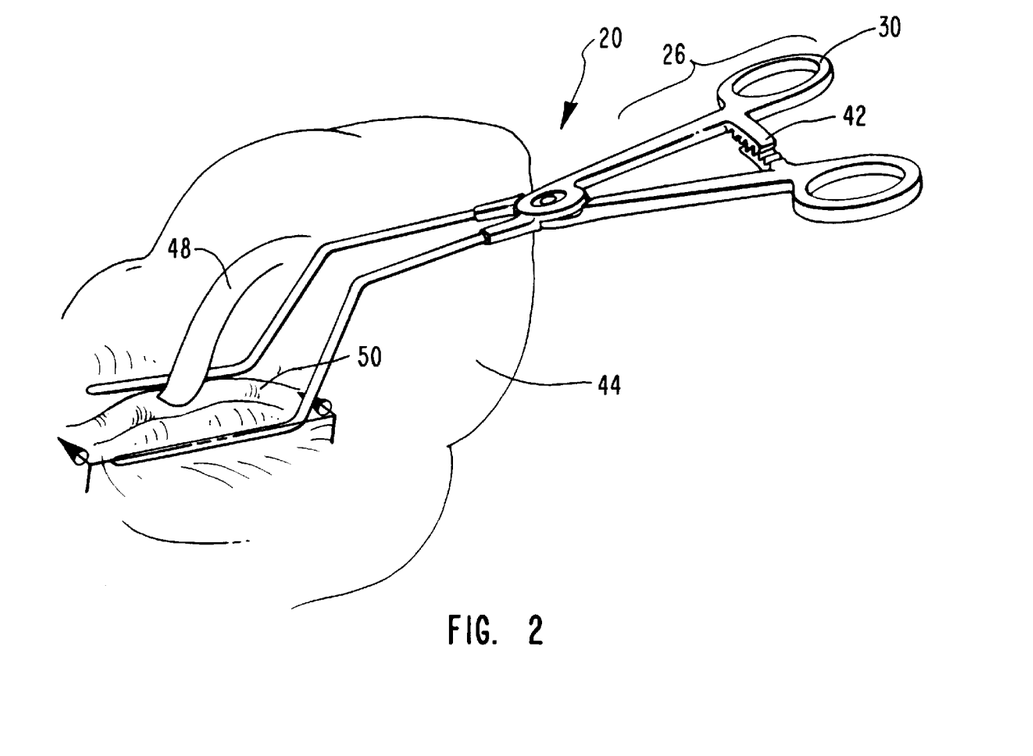
FIG. 2 is a perspective view of the embodiment from FIG. 1.

The surgeon then locks in place the handle 26 via the preferred ratchet mechanism 42 to hold the specific articulation of the surgical stabilizer. With the tissue thus isolated and immobilized, the surgeon may then graft the bypass vessel 48 to the coronary artery 50 just distal to the stenosis.

A preferred feature of the present invention provides additional stabilization of the surgical site through the use of suction. The use of suction allows the coronary artery and surrounding fascia to be retracted. Thus, while the cardiac muscle functions normally, a surgeon can immobilize and isolate the requisite coronary tissue away from the beating heart, without substantially interrupting the blood flowing therethrough.

Figure 4:
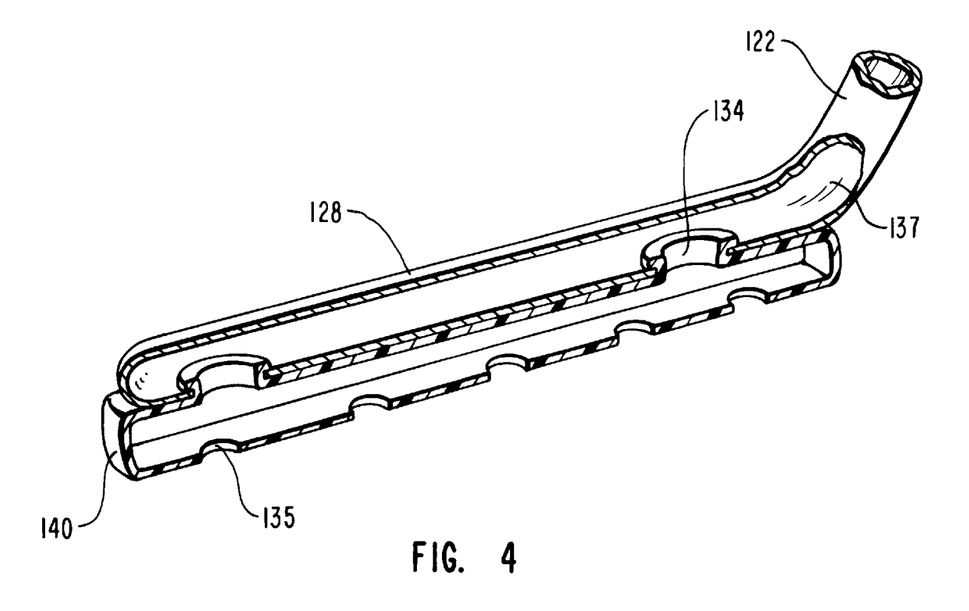
FIG. 4 is a partial cross-sectional view of an alternate embodiment of the present invention.
Figure 5:
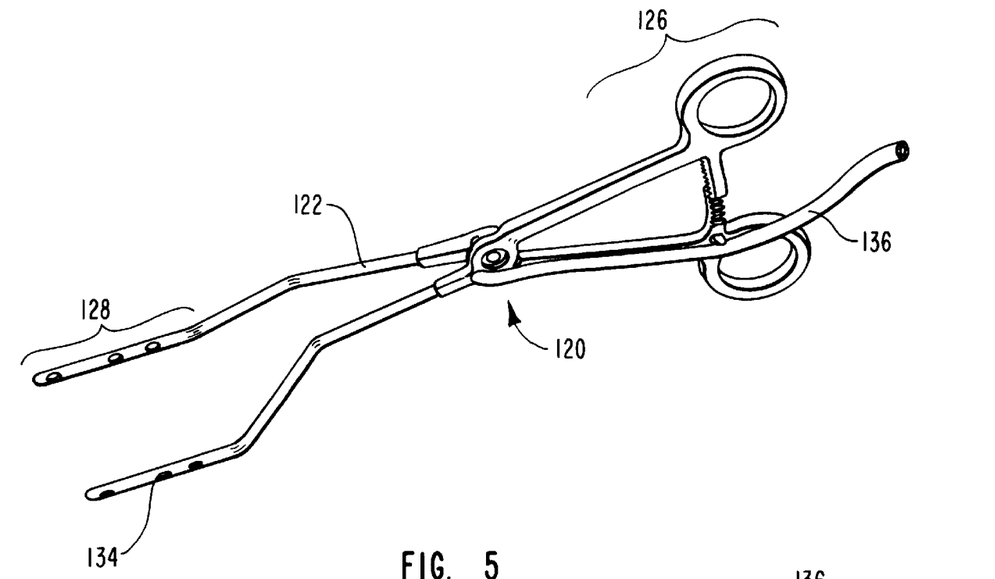
FIG. 5 is a perspective view of an alternate embodiment of the present invention.

As illustrated in FIG. 5, it is a preferred feature of the present invention that a vacuum mechanism, illustrated by tubing 136, is attached to the surgical stabilizer 120. A vacuum channel 137, illustrated in cross section in FIG. 4, preferably extends through the handle (not shown in FIG. 4) and through the legs 122 to the feet 128. The indentations 134 on the posterior surface 132 of the feet then serve as inlet openings for the air flow supplied through the vacuum channel by the vacuum mechanism. In addition, when disposable traction devices 140 are employed as illustrated in FIG. 4, the vacuum mechanism suctions through these devices via suction openings 135.

The present invention is additionally directed to a method for using the surgical stabilizer with suction. In a preferred embodiment illustrated in FIG. 6, the surgical stabilizer 120, in conjunction with vacuum tubing 136, is utilized to retract the tissue proximal to a stenotic coronary artery. The surgeon selectively isolates and immobilizes the tissue by manipulating the surgical stabilizer to articulate the tissue apart or push it together, as per his or her preference, or per the requirements of the surgical situation.

Figure 6:
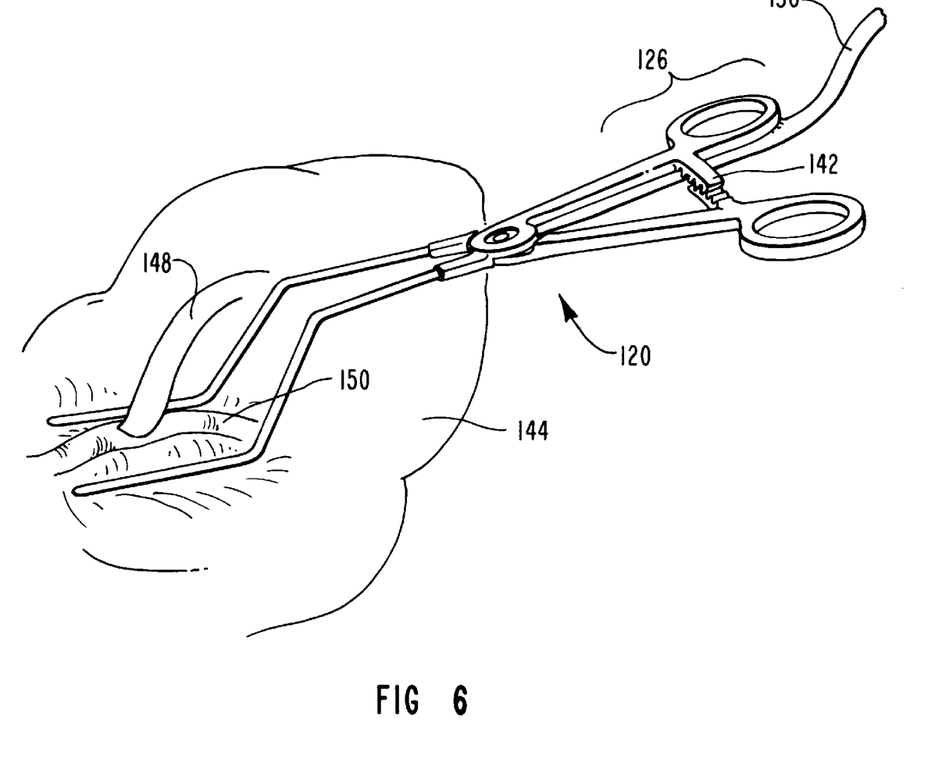
FIG. 6 is posterior perspective view of the embodiment form FIG. 5.

The surgeon then may lock in place the handle 126 via the preferred ratchet mechanism 142 to hold the specific articulation of the surgical stabilizer. With the tissue thus isolated and immobilized, the surgeon may then graft the bypass vessel 148 to the coronary artery 150 just distal to the stenosis, while the heart 144 continues normal beating below.

It is another feature of the present invention that the surgical stabilizer can be of unitary construction. FIG. 7 illustrates such an embodiment of surgical stabilizer 220 incorporating a suction mechanism 236. In this embodiment, a non-hinged member such as sleeve 238 serves as the means for articulation of the legs. In the normal position of sleeve 238 as illustrated in FIG. 7, legs 222 are biased open. In order to articulate the legs closed, sleeve 238 is moved downward along the apparatus as illustrated in FIG. 8. It will be appreciated in view of the teachings herein, however, that the sleeve embodiment could also be used without the suction mechanism.

Figure 9:
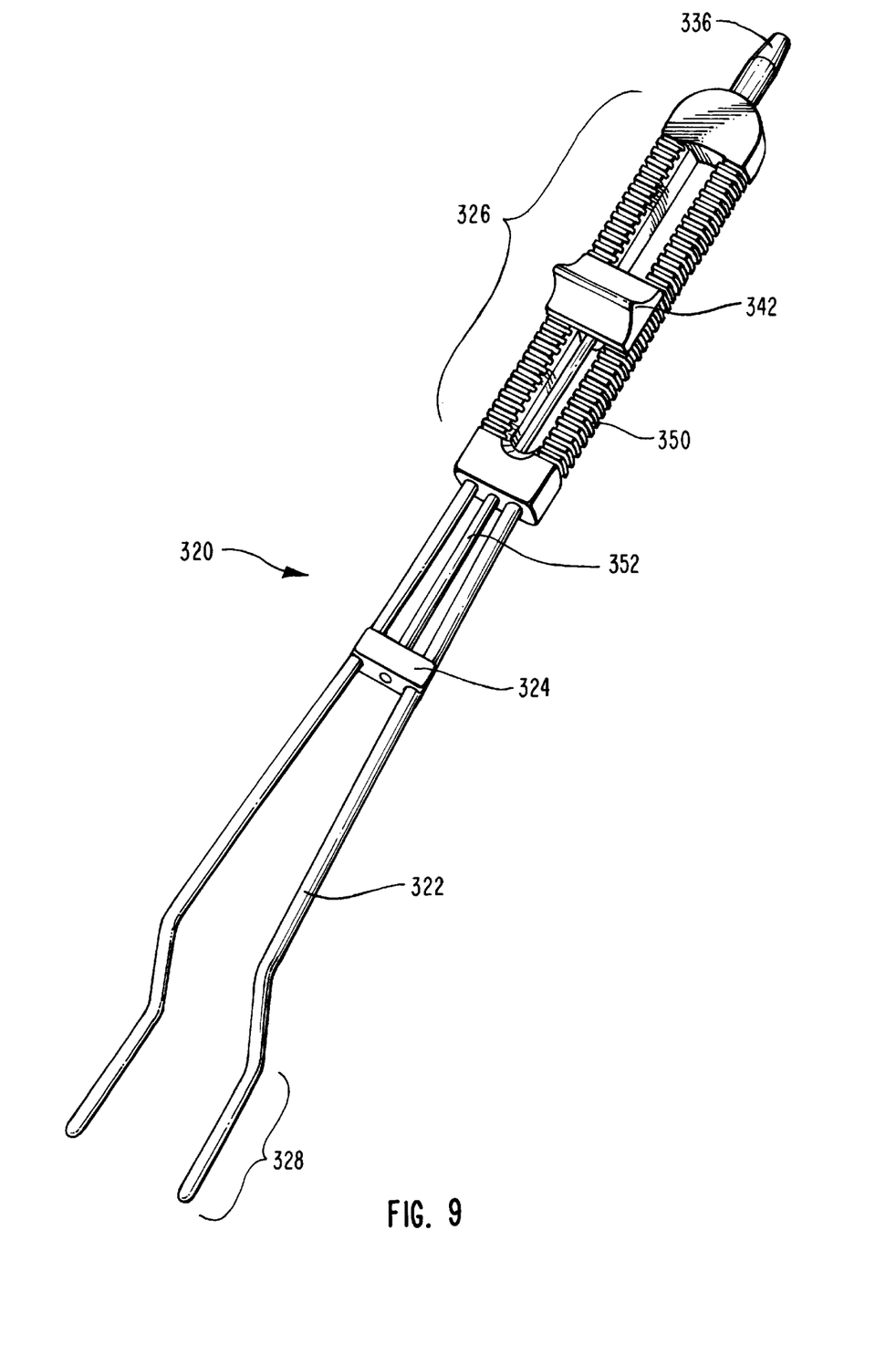
FIG. 9 is an anterior view of an alternate embodiment of the present invention.
Figure 10:
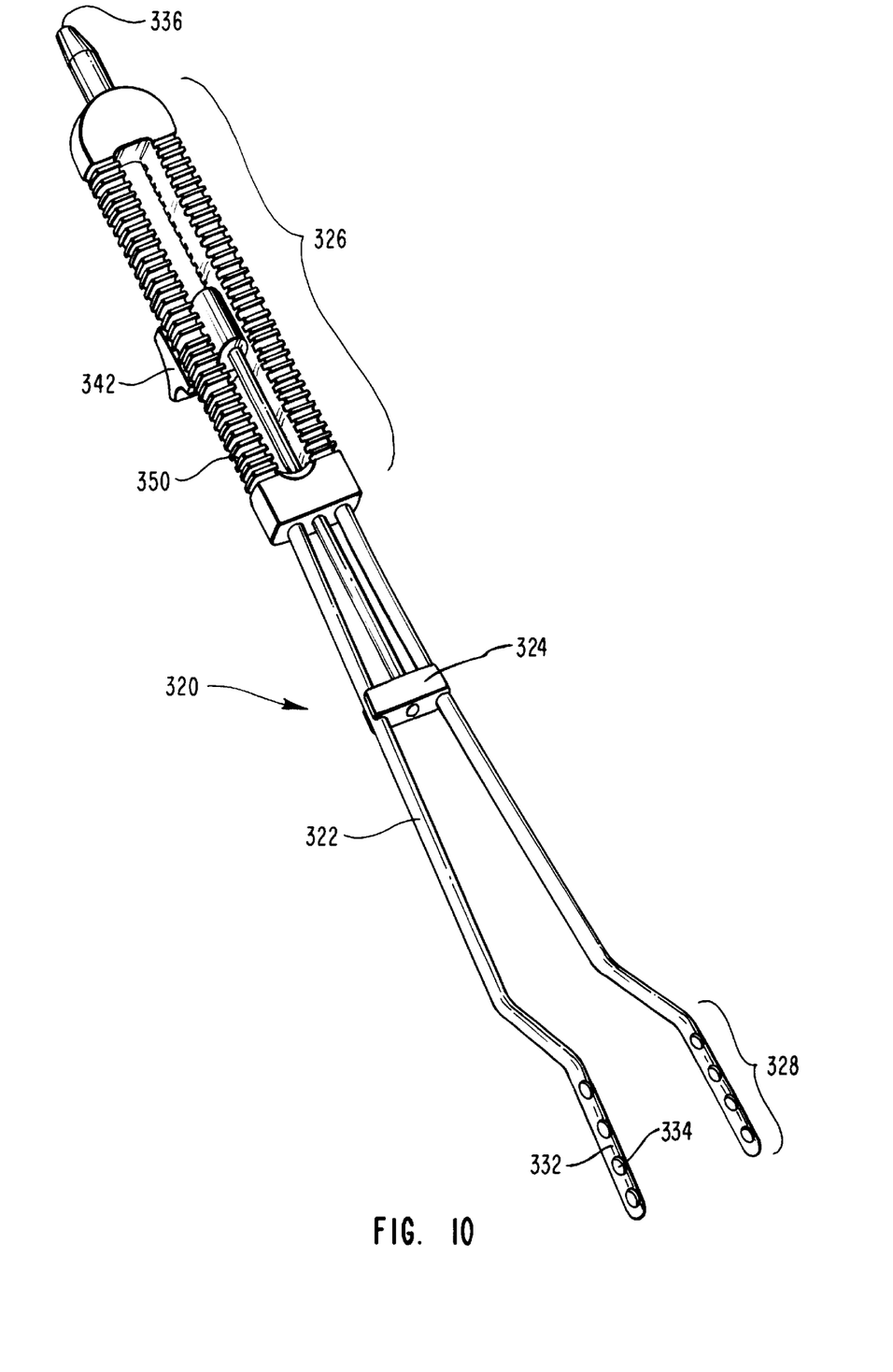
FIG. 10 is a posterior view of the embodiment from FIG. 9.

Another preferred embodiment of the present invention is illustrated in FIGS. 9 and 10. The surgical stabilizer 320 depicted in FIGS. 9 and 10 comprises two legs 322, articulation sleeve 324, and handle 326.

The legs 322 slant downward and terminate distally in feet 328. It is a feature of the present invention that the feet 328 may be utilized to tamponade, or compress, the cardiac tissue. FIG. 10 additionally illustrates the posterior surface 332 of feet 328 which comprises a plurality of indentations 334. The indentations provide traction on the posterior surface of the feet and also serve as suction openings when a vacuum or other suction mechanism is utilized with this embodiment of the present invention.

As illustrated in FIGS. 9 and 10, legs 322 connect proximally with handle 326. Handle 326 preferably allows one-handed manipulation of the surgical stabilizer. Handle 326 terminates proximally in vacuum opening 336 which allows fluid communication between the surgical stabilizer and a vacuum or other suction mechanism. In one embodiment of the present invention, tubing connects vacuum opening to a vacuum pump. In addition, handle 326 and legs 322 comprise channels, not illustrated, which run through handle and into legs such that indentations are in fluid communication with vacuum opening.

Handle 326 preferably includes a plurality of detents 350 running the length thereof. Detents 350 work in concert with articulation member 342, also provided on handle 326. Specifically, each detent serves as a stopping point for articulation member 342.

It is an additional feature of the present invention that articulation member 342 may be operated with only one hand. In a preferred embodiment illustrated in FIG. 9, articulation member is shaped to facilitate manipulation with a user's thumb.

Articulation member 342 works in concert with articulation sleeve 324 via connector rod 352, which connects articulation member 342 to articulation sleeve 324. Articulation sleeve 324 serves as the means for articulation of the legs. Articulation member 342 in turn serves as the means for retaining legs 322 in an articulated open or closed position via articulation sleeve 324 and connector rod 352.

As articulation member is moved proximally along the detents on the handle, that is, toward the vacuum opening, the legs are articulated open. As the articulation member is moved distally along the detents on the handle, that is, toward the legs of the device, the legs are articulated closed. The legs are thus slightly biased toward an open articulation, and articulation sleeve essentially pulls the legs together.

It should also be understood that the aforementioned methods are in no way limiting to the scope of the present invention. Alternate methods for using the surgical stabilizer would also be envisioned by the present invention. In addition, the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for isolating and immobilizing tissue at a cardiac surgical site while improving surgical presentation thereof, comprising:

a. at least two leg extensions, said leg extensions terminating in feet projections comprising posterior surfaces, said posterior surfaces further comprising means for promoting traction of said feet projections on cardiac tissue, said means for promoting traction further comprising a plurality of indentations, and wherein said plurality of indentations interconnect with disposable traction devices for further promoting traction of said feet projections on cardiac tissue;

b. articulation means for uniform articulation of said at least two leg extensions; and c. handle means for manipulation of said at least two leg extensions in concert with said articulation means.

2. An apparatus for isolating and immobilizing tissue at a cardiac surgical site while improving surgical presentation thereof, comprising:

a. at least two leg extensions, said leg extensions terminating in feet projections comprising posterior surfaces, said posterior surfaces further comprising means for promoting traction of said feet projections on cardiac tissue, said means for promoting traction further permitting fluid flow through said feet projections and said leg extensions;

b. articulation means for uniform articulation of said at least two leg extensions;

c. handle means for manipulation of said at least two leg extensions in concert with said articulation means; and d. a vacuum channel extending through said leg extensions and terminating distally at said posterior surface of said feet projections.

3. An apparatus as recited in claim 2, wherein said means for promoting traction of said feet projections on cardiac tissues comprise a plurality of indentations.

4. An apparatus as recited in claim 3, wherein said plurality of indentations connect with disposable traction devices for further promoting traction of said feet projections on cardiac tissue.

5. An apparatus as recited in claim 4, wherein said disposable traction devices further comprise inlet openings for air flow into said vacuum channel.

6. An apparatus a s recited in claim 2, wherein said means for uniform articulation of said at least two legs comprises an articulation joint.

7. An apparatus as recited in claim 2, wherein said means for uniform articulation of said at least two legs comprises a sleeve.

8. An apparatus as recited in claim 2, wherein said handle means further comprises means for retaining said at least two leg extensions in an articulated position.

9. An apparatus as recited in claim 8, wherein said means for retaining said at least two leg extensions in an articulated position is a ratchet mechanism.

10. An apparatus as recited in claim 8, wherein said means for retaining said at least two leg extensions in an articulated position is a mechanical stop.

11. An apparatus as recited in claim 8, wherein said articulated position is substantially opened.

12. An apparatus as recited in claim 8, wherein said articulated position is substantially closed.

13. A method for selectively isolating and immobilizing cardiac tissue, and improving surgical presentation thereof, comprising the steps of:

a. obtaining an apparatus for isolating and immobilizing cardiac tissue comprising:

1) at least two leg extensions; said leg extensions terminating in feet projections comprising posterior surfaces, said posterior surfaces further comprising means for promoting traction of said feet projections on cardiac tissue, said means for promoting traction further permitting fluid flow through said feet projections and said leg extensions;

2) articulation means for uniform articulation of said at least two leg extensions;

3) handle means for manipulation of said at least two leg extensions in concert with said articulation means; and 4) a vacuum channel extending through said leg extensions and terminating distally at said posterior surface of said feet projections;

b. manipulating said at least two leg extensions in concert with said vacuum channel for selective retraction of cardiac tissue;

c. selectively articulating said cardiac tissue; and d. locking said articulation means in an articulated position.

14. An apparatus for isolating and immobilizing tissue at a cardiac surgical site while improving surgical presentation thereof, comprising:

a. at least two leg extensions, said leg extensions terminating in feet projections comprising posterior surfaces, said posterior surfaces further comprising a plurality of indentations for promoting traction of the feet on cardiac tissue, and wherein said plurality of indentations interconnect with disposable traction devices for further promoting traction of said feet projections on cardiac tissue;

b. an articulation joint capable of providing uniform articulation of said at least two leg extensions; and c. a handle designed for manipulation of said at least two leg extensions in concert with said articulation joint.

15. An apparatus for isolating and immobilizing tissue at a cardiac surgical site while improving surgical presentation thereof, comprising:

a. at least two leg extensions, said leg extensions terminating in feet projections comprising posterior surfaces, said posterior surfaces further comprising indentations for promoting traction of said feet projections on cardiac tissue, said indentations further permitting fluid flow through said feet projections and said leg extensions;

b. an articulation joint capable of providing uniform articulation of said at least two leg extensions;

c. a handle designed for manipulation of said at least two leg extensions in concert with said articulation joint; and d. a vacuum channel extending through said leg extensions and terminating distally at said posterior surface of said feet projections.

16. An apparatus as recited in claim 15, wherein said plurality of indentations connect with disposable traction devices for further promoting traction of said feet projections on cardiac tissue.

17. An apparatus as recited in claim 16, wherein said disposable traction devices further comprise inlet openings for air flow into said vacuum channel.

18. An apparatus as recited in claim 15, wherein said handle further comprises a ratchet mechanism designed for retaining said at least two leg extensions in an articulated position.

19. An apparatus as recited in claim 18, wherein said articulated position is substantially opened.

20. An apparatus as recited in claim 18, wherein said articulated position is substantially closed.

21. A method for selectively isolating and immobilizing cardiac tissue, and improving surgical presentation thereof, comprising the steps of:

a. obtaining an apparatus for isolating and immobilizing cardiac tissue comprising:

1) at least two leg extensions; said leg extensions terminating in feet projections comprising posterior surfaces, said posterior surfaces further comprising indentations for promoting traction of said feet projections on cardiac tissue, said indentations further permitting fluid flow through said feet projections and said leg extensions;

2) an articulation joint capable of providing uniform articulation of said at least two leg extensions;

3) a handle designed for manipulation of said at least two leg extensions in concert with said articulation joint; and 4) a vacuum channel extending through said leg extensions and terminating distally at said posterior surface of said feet projections;

b. manipulating said at least two leg extensions in concert with said vacuum channel for selective retraction of cardiac tissue;

c. selectively articulating said cardiac tissue; and d. locking said articulation joint in an articulated position.

* * * * *